US006884578B2

(12) United States Patent
Warrington et al.

(10) Patent No.: US 6,884,578 B2
(45) Date of Patent: Apr. 26, 2005

(54) GENES DIFFERENTIALLY EXPRESSED IN SECRETORY VERSUS PROLIFERATIVE ENDOMETRIUM

(75) Inventors: Janet A. Warrington, Los Altos, CA (US); Mamatha Mahadevappa, Cupertino, CA (US)

(73) Assignee: Affymetrix, Inc., Santa Clara, CA (US)

( * ) Notice: Subject to any disclaimer, the term of this patent is extended or adjusted under 35 U.S.C. 154(b) by 0 days.

(21) Appl. No.: 09/734,752

(22) Filed: Dec. 11, 2000

(65) Prior Publication Data

US 2001/0044104 A1 Nov. 22, 2001

Related U.S. Application Data

(60) Provisional application No. 60/240,678, filed on Oct. 13, 2000, provisional application No. 60/231,367, filed on Sep. 8, 2000, and provisional application No. 60/193,719, filed on Mar. 31, 2000.

(51) Int. Cl.[7] .......................... C12Q 1/68; C07H 21/04
(52) U.S. Cl. .......................... 435/6; 536/23.1; 536/23.5
(58) Field of Search .......................... 435/6, 91.1, 91.2, 435/7.1, 69.1; 536/23.1, 23.5, 24.3, 23.4, 24.1; 436/501

(56) References Cited

U.S. PATENT DOCUMENTS

| | | | | |
|---|---|---|---|---|
| 5,143,854 | A | | 9/1992 | Pirrung et al. ............... 436/518 |
| 5,384,261 | A | | 1/1995 | Winkler et al. .............. 436/518 |
| 5,424,186 | A | | 6/1995 | Fodo et al. ...................... 435/6 |
| 5,445,934 | A | | 8/1995 | Fodor et al. .................... 435/6 |
| 5,631,734 | A | | 5/1997 | Stern et al. ................... 356/317 |
| 5,677,195 | A | | 10/1997 | Winkler et al. .............. 436/518 |
| 5,708,153 | A | | 1/1998 | Dower et al. ............... 536/22.1 |
| 5,733,729 | A | | 3/1998 | Lipschutz et al. .............. 435/6 |
| 5,744,305 | A | | 4/1998 | Fodor et al. .................... 435/6 |
| 5,770,358 | A | | 6/1998 | Dower et al. ................... 435/6 |
| 5,770,722 | A | | 6/1998 | Lockhart et al. ........... 536/25.3 |
| 5,800,992 | A | | 9/1998 | Fodor et al. .................... 435/6 |
| 5,854,401 | A | * | 12/1998 | Lessey ..................... 530/388.1 |
| 5,856,174 | A | | 1/1999 | Lipschutz et al. ........ 435/286.5 |
| 5,874,219 | A | | 2/1999 | Rava et al. ..................... 435/6 |
| 5,922,591 | A | | 7/1999 | Anderson et al. ......... 435/287.2 |
| 5,981,956 | A | | 11/1999 | Stern ........................ 250/458.1 |
| 6,013,440 | A | | 1/2000 | Lipschutz et al. ............. 435/6 |
| 6,020,135 | A | | 2/2000 | Levine et al. .................. 435/6 |
| 6,025,601 | A | | 2/2000 | Trulson et al. ........... 250/461.2 |
| 6,033,850 | A | | 3/2000 | Purvis ............................ 435/6 |
| 6,033,860 | A | * | 3/2000 | Lockhart et al. ............... 435/6 |
| 6,040,138 | A | | 3/2000 | Lockhart et al. ............... 435/6 |
| 6,040,193 | A | | 3/2000 | Winkler et al. .............. 436/180 |
| 6,218,122 | B1 | * | 4/2001 | Friend et al. ................... 435/6 |
| 6,440,445 | B1 | * | 8/2002 | Nowak et al. ............... 424/423 |
| 2002/0106662 | A1 | * | 8/2002 | Mutter ........................... 435/6 |
| 2002/0127555 | A1 | * | 9/2002 | Baban et al. ................... 435/6 |

FOREIGN PATENT DOCUMENTS

WO 98/53319 11/1998

OTHER PUBLICATIONS

Srinivasan et al. (Clinical Cancer Research (1999) 5: 2877–2883).*
Abu–Jawdeh et al. (Laboratory Investigation (1999) 79(4): 439–447).*
Florio et al. (Human Reproduction (1998) 13(9): 2606–2611).*
Alizadeh et al., "Distinct types of diffuse large B–cell lymphoma identified by gene expression profiling", *Nature*, vol. 403, Feb. 2000, pps. 503–511.
Alon et al., "Broad patterns of gene expression revealed by clustering analysis of tumor and nornal colon tissues probed by oligonucleotide arrays", *Proc. Natl. Acad. Sci. USA*, vol. 96, Jun. 1999, pps. 6745–6750.
Chu et al., "The Transcriptional Program of Sporulation in Budding Yeast", *Science*, vol. 282, Oct. 1998, pps. 699–705.
Chee et al., "Accessing Genetic Information with High–Density DNA Arrays", *Science*, vol. 274, No. 5287, Oct. 25, 1966, pps. 610–614.
Cho et al., "A Genome–Wide Transcriptional Analysis of the Miotic Cell Cycle", *Molecular Cell*, vol. 2, Jul. 1998, pps. 65–73.
DeRisi et al., "Exploring the Metabolic and Genetic Control of Gene Expression on a Genomic Scale", *Science*, vol. 278, Oct. 24, 1997, pps. 680–686.
Ferea et al., "Observing the living genome", *Current Opinion in Genetics & Developments*, 1999, pps. 9:715–722.
Gray et al., "Exploiting Chemical Libraries, Structure and Genomics in the Search for Kinase Inhibitors", *Science*, vol. 281, Jul. 24, 1998, pps. 533–538.
Golub et al., "Molecular Classification of Cancer: Class Discovery and Class Predicition by Gene Expression Monitoring", *Science*, vol. 286, Oct. 15, 1999, pps. 531–537.
Holstege et al., "Dissecting the Regulatory Circuitry of a Eukaryotic Genome", *Cell*, vol. 95, Nov. 25, 1998, pps. 717–728.
Harrington et al., "Monitoring gene expression using DNA microarrays", *Current Opinion in Microbiology*, 2000, pps. 3:285–291.

(Continued)

Primary Examiner—Carla J. Myers
Assistant Examiner—Alexander H. Spiegler
(74) Attorney, Agent, or Firm—Sandra E. Wells; Wei Zhou; Philip L. McGarrigle

(57) ABSTRACT

The present invention compares expression profiles from matched samples to identify differential gene expression. Samples are matched according to physiological, pharmacological and/or disease state. Comparison of matched samples eliminates gene expression differences that are the result of changes in variables that are not of interest. The gene expression differences that remain can be attributed with a high degree of confidence to the unmatched variation. The gene expression differences thus identified can be used for example to diagnose disease, identify physiological state, design drugs, and monitor therapies.

1 Claim, No Drawings

OTHER PUBLICATIONS

Iyer et al., "The Transcriptional Program in the Response of Human Fibroblasts to Serum", *Science*, vol. 283, Jan. 1, 1999, pps. 83–87.

Lee et al., "Gene Expression Profile of Aging and its Retardation by Caloric Restriction", *Science*, vol. 285, Aug. 27, 1999, pps. 1390–1393.

Lockhart, "Mutant yeast on drugs", *Natural Medicine*, vol. 4, No. 11, Nov. 1998, pps. 1235–1236.

Lockhart et al., "Expression monitoring by hybridization to high–density oligonucleotide arrays", *Nature Biotechnology*, vol. 14, Dec. 1996, pps. 1675–1680.

Madhani et al., "Effectors of a development mitogen–activated protein kinase cascade revealed by expression signatures of signaling mutants", *Proc. Natl. Acad. Sci. USA*, vol. 96, No. 22, Oct. 26, 1999 pps. 12530–12535.

Perou et al., "Distinctive gene expression patterns in human mammary epithelial cells and breast cancers", *Proc. Natl. Acad. Sci. USA*, vol. 96, Aug. 1999, pps. 9212–9217.

Salamonsen et al., "Current concepts of the mechanisms of menstruation", *Bailliered Best Pract Rest Clin Obstet Gynaecol*, Jun. 1999, pps. 13(2): 161–179.

Tabibzadeh et al., "From Endometrail Receptivity to Infertility", *Seminars in Repro Endocrinology*, vol. 17, No. 3, 1999, pps. 197–203.

Velculescu et al., "Characterization of the Yeast Transcriptome", *Cell*, vol. 88, Jan. 24, 1997, pps. 243–251.

Winzeler et al., "Functional Characterization of the S. cerevisiae Genome by Gene Deletion and Parallel Analysis", *Science*, vol. 285, Aug. 6, 1999, pps. 901–906.

Wodicka et al., "Genome–wide expression monitoring in *Saccharomyces cerevisiae*", *Nature Biotechnology*, vol. 15, Dec. 1997, pps. 1359–1367.

Zhang et al., "Gene Expression Profiles in Normal and Cancer Cells", *Science*, vol. 276, May 23, 1997, pps. 1268–1272.

Zhu et al., "Cellular gene expression altered by human cytomegalovirus: Global monitoring with oligonucleotide arrays", *Proc. Natl. Acad. Sci. USA*, vol. 95, Nov. 1998, pps. 14470–14475.

* cited by examiner

GENES DIFFERENTIALLY EXPRESSED IN SECRETORY VERSUS PROLIFERATIVE ENDOMETRIUM

RELATED APPLICATIONS

This application is related to and claims the priority date of U.S. provisional application entitled Genes Differentially Expressed in Secretory vs Proliferative Endometrium, Ser. No. 60/193,719 filed on Mar. 31, 2000, U.S. provisional application entitled Comparison of Matched Expression Profiles, Ser. No. 60/231,367, filed Sep. 8, 2000, and U.S. provisional application entitled Genes Differentially Expressed in Secretory Versus Proliferative Endometrium, Ser. No. 60/240,678, filed on Oct. 13, 2000, all of which are hereby incorporated by reference in their entirety for all purposes.

BACKGROUND

Many cellular events and processes are characterized by altered expression levels of one or more genes. Differences in gene expression correlate with many physiological processes such as cell cycle progression, cell differentiation and cell death. Changes in gene expression patterns also correlate with changes in disease or pharmacological state. For example, the lack of sufficient expression of functional tumor suppressor genes and/or the over expression of oncogene/protooncogenes could lead to tumorgenesis (Marshall, *Cell,* 64: 313–326 (1991); Weinberg, Science, 254: 1138–1146 (1991), incorporated herein by reference for all purposes). Thus, changes in the expression levels of particular genes (e.g. oncogenes or tumor suppressors) serve as signposts for different physiological, pharmacological and disease states.

Gene expression profiles produce a snapshot that reflects the biological status of the sample, but in many circumstances biological status will reflect more than one characteristic of the sample. For example, when comparing tumor samples from two patients, there will be changes that correlate with differences between the states of the tumors as well as changes that correlate with the different physiological states of the two patients. One aspect of the current invention is directed at identifying genes that are differentially expressed between two biological states as being further correlated with disease, physiological or pharmacological state.

SUMMARY OF THE INVENTION

The present invention is a method to analyze samples that differ from one another in multiple variables in such a way as to account for the variables and to focus on elements that are under investigation, such as disease state for example. Comparison of matched samples eliminates gene expression differences that are the result of changes in variables that are not of interest. The gene expression differences that remain can be attributed with a high degree of confidence to the unmatched variation. The gene expression differences thus identified can be used, for example, to diagnose disease, identify physiological state, design drugs, and monitor therapies.

DETAILED DESCRIPTION OF THE PREFERRED EMBODIMENTS

This application relies on, and cites the disclosure of other patent applications and literature references. These documents are hereby incorporated by reference in their entireties for all purposes. The practice of the present invention may employ, unless otherwise indicated, conventional techniques of organic chemistry, polymer technology, molecular biology (including recombinant techniques), cell biology, biochemistry, and immunology, which are within the skill of the art. Such conventional techniques include polymer array synthesis, hybridization, ligation, detection of hybridization using a label. Specific illustrations of suitable techniques can be had by reference to the example hereinbelow. However, other equivalent conventional procedures can, of course, also be used. Such conventional techniques can be found in standard laboratory manuals such as *Genome Analysis: A Laboratory Manual Series* (Vols. I–IV), *Using Antibodies: A Laboratory Manual, Cells: A Laboratory Manual, PCR Primer: A Laboratory Manual,* and *Molecular Cloning: A Laboratory Manual* (all from Cold Spring Harbor Laboratory Press), all of which are herein incorporated in their entirety by reference.

This section presents a detailed description of the preferred invention and its application. This description is by way of several exemplary illustrations, in increasing detail and specificity, and of the general methods of this invention. These examples are non-limiting, and related variants that will be apparent to one of skill in the art are intended to be encompassed by the appended claims. Following these examples are descriptions of embodiments of the data gathering steps that accompany the general methods.

DESCRIPTION OF CONCEPTS

Nucleic acids according to the present invention may include any polymer or oligomer of pyrimidine and purine bases, preferably cytosine, thymine, and uracil, and adenine and guanine, respectively. See Albert L. Lehninger, PRINCIPLES OF BIOCHEMISTRY, at 793–800 (Worth Pub. 1982). Indeed, the present invention contemplates any deoxyribonucleotide, ribonucleotide or peptide nucleic acid component, and any chemical variants thereof, such as methylated, hydroxymethylated or glucosylated forms of these bases, and the like. The polymers or oligomers may be heterogeneous or homogeneous in composition, and may be isolated from naturally-occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states. Oligonucleotide and polynucleotide are included in this definition and relate to two or more nucleic acids in a polynucleotide.

Peptide: A polymer in which the monomers are alpha amino acids and which are joined together through amide bonds, alternatively referred to as a polypeptide. In the context of this specification it should be appreciated that the amino acids may be, for example, the L-optical isomer or the D-optical isomer. Peptides are often two or more amino acid monomers long, and often 4 or more amino acids long, often 5 or more amino acids long, often 10 or more amino acids long, often 15 or more amino acids long, and often 20 or more amino acid monomers long, for example. Standard abbreviations for amino acids are used (e.g., P for proline). These abbreviations are included in Stryer, Biochemistry, Third Ed., 1988, which is incorporated herein by reference for all purposes.

Array: An array comprises a solid support with peptide or nucleic acid probes attached to said support. Arrays typically comprise a plurality of different nucleic acid or peptide probes that are coupled to a surface of a substrate in different, known locations. These arrays, also described as "microarrays" or colloquially "chips" have been generally described in the art, for example, U.S. Pat. Nos. 5,143,854, 5,445,934, 5,744,305, 5,677,195, 6,040,193, 5,424,186 and Fodor et al., Science, 251:767–777 (1991). Each of which is incorporated by reference in its entirety for all purposes. These arrays may generally be produced using mechanical synthesis methods or light directed synthesis methods which incorporate a combination of photolithographic methods and solid phase synthesis methods. Techniques for the synthesis of these arrays using mechanical synthesis methods are described in, e.g., U.S. Pat. No. 5,384,261, incorporated herein by reference in its entirety for all purposes. Although a planar array surface is preferred, the array may be fabricated on a surface of virtually any shape or even a multiplicity of surfaces. Arrays may be peptides or nucleic acids on beads, gels, polymeric surfaces, fibers such as fiber optics, glass or any other appropriate substrate, see U.S. Pat. Nos. 5,770,358, 5,789,162, 5,708,153, 6,040,193 and 5,800, 992, which are hereby incorporated in their entirety for all purposes. Arrays may be packaged in such a manner as to allow for diagnostics or other manipulation of an all inclusive device, see for example, U.S. Pat. Nos. 5,856,174 and 5,922,591 incorporated in their entirety by reference for all purposes. See also U.S. patent application Ser. No. 09/545, 207, filed Apr. 7, 2000 for additional information concerning arrays, their manufacture, and their characteristics. It is hereby incorporated by reference in its entirety for all purposes.

Physiological State or Physiological Status: According to the present invention, a physiological state refers to any normal biological state of a cell or organism. The parameters that are considered in determining physiological state include but are not limited to age, gender, ethnic origin, and reproductive state, which includes, but is not limited to menstrual state, post-partum, pregnancy, lactation, and nulliparity. For the purposes of this invention the physiological state may be determined by a single indicator. For example, the age of a patient may be the only indicator of physiological state used to categorize a reference sample. Preferably several indicators of physiological state will be used to categorize a reference sample. Methods to determine the physiological state of a sample include but are not limited to measuring the abundance and/or activity of cellular constituents (expression profile, genotyping), morphological phenotype, or interview of the subject.

Physiological state can refer to, but is not limited to, the physiological state of an organism, an organ, a tissue, a collection of cells or an individual cell. In a preferred embodiment, the physiological state refers to the physiological state of a whole organism. In another embodiment physiological state refers to the physiological state of a tissue, for example the physiological state of the uterine lining.

Disease State or Disease Status: In addition to a physiological state, a sample may or may not be affected with a disease state. According to the present invention, a disease state refers to any abnormal biological state of a cell. This includes but is not limited to an interruption, cessation or disorder of body functions, systems or organs. In general, a disease state will be detrimental to a biological system. With respect to the present invention, any biological state, such as a premalignancy state, that is associated with a disease or disorder is considered to be a disease state. A pathological state is the equivalent of a disease state.

Disease states can be further categorized into different levels of disease state. As used in the present invention, the level of a disease or disease state is an arbitrary measure reflecting the progression of a disease or disease state. Generally, a disease or disease state will progress through a plurality of levels or stages, wherein the affects of the disease become increasingly severe. The level of a disease state may be impacted by the physiological state of the sample.

Therapy or Therapeutic Regimen: In order to alleviate or alter a disease state, a therapy or therapeutic regimen is often undertaken. A therapy or therapeutic regimen, as used herein, refers to a course of treatment intended to reduce or eliminate the affects or symptoms of a disease. A therapeutic regimen will typically comprise, but is not limited to, a prescribed dosage of one or more drugs or surgery. Therapies, ideally, will be beneficial and reduce the disease state but in many instances the effect of a therapy will have non-desirable effects as well. The effect of therapy will also be impacted by the physiological state of the sample.

Pharmacological State or Pharmacological Status: Treatment with drugs may affect the pharmacological state of a sample. The pharmacological state of a sample relates to changes in the biological status following drug treatment. Some of the changes following drug treatment or surgery may be relevant to the disease state. Some may be unrelated-side effects of the therapy. Some will be specific to physiological state. Indicators of pharmacological state include, but are not limited to, duration of therapy, types and doses of drugs prescribed, degree of compliance with a given course of therapy, and/or unprescribed drugs ingested.

Biological State or Biological Status: According to the present invention, the biological state of a sample refers to the state of a collection of cellular constituents or any other observable phenotype, which is sufficient to characterize the sample for an intended purpose. The biological state reflects the physiological state of a sample, any disease state that affects the sample and the pharmacological state if applicable. Some methods to determine the biological state of a sample include but are not limited to measuring the abundance and/or activity of cellular constituents, characterizing according to morphological phenotype or a combination of the above methods.

The biological status of a sample can be measured or observed by interrogating the abundances and/or activities of a collection of cellular constituents. In various embodiments, this invention includes making such measurements and/or observations on different collections of cellular constituents.

Expression Profile: One measurement of cellular constituents that is particularly useful in the present invention is the expression profile. As used herein, an "expression profile" comprises measurement of the relative abundance of a plurality of cellular constituents. Such measurements may include, RNA or protein abundances or activity levels. The expression profile can be a measurement for example of the transcriptional state or the translational state. See U.S. Pat. Nos. 6,040,138, 5,800,992, 6,020135, 6,033,860 and U.S. Ser. No. 09/341,302 which are hereby incorporated by reference in their entireties.

Transcriptional State: The transcriptional state of a sample includes the identities and relative abundances of the RNA species, especially mRNAs present in the sample. Preferably, a substantial fraction of all constituent RNA species in the sample are measured, but at least, a sufficient fraction is measured to characterize the state of the sample. The transcriptional state is the currently preferred aspect of the biological state measured in this invention. It can be conveniently determined by measuring transcript abundances by any of several existing gene expression technologies.

Translational State: Translational state includes the identities and relative abundances of the constituent protein species in the sample. As is known to those of skill in the art, the transcriptional state and translational state are related.

The gene expression monitoring system, in a preferred embodiment, may comprise a nucleic acid probe array (such as those described above), membrane blot (such as used in hybridization analysis such as Northern, Southern, dot, and the like), or microwells, sample tubes, gels, beads or fibers (or any solid support comprising bound nucleic acids). See U.S. Pat. Nos. 5,770,722, 5,874,219, 5,744,305, 5,677,195 and 5,445,934, which are expressly incorporated herein by reference. See also Examples, infra. The gene expression monitoring system may also comprise nucleic acid probes in solution.

The gene expression monitoring system according to the present invention may be used to facilitate a comparative analysis of expression in different cells or tissues, different subpopulations of the same cells or tissues, different physiological states of the same cells or tissue, different developmental stages of the same cells or tissue, or different cell populations of the same tissue.

Differentially Expressed: The term differentially expressed as used herein means that the measurement of a cellular constituent varies in two or more samples. The cellular constituent can be either upregulated in the experimental relative to the reference or downregulated in the experimental relative to the reference. Differential gene expression can also be used to distinguish between cell types or nucleic acids. See U.S. Pat. No. 5,800,992.

General

The comparison of gene expression profiles from an experimental sample and a reference sample to identify genes that are differentially expressed between two or more different biological states in the same cell type has become a powerful diagnostic and prognostic tool. Genes identified through this method can be used as markers for the presence or level of a disease, as prognostic devices to monitor efficacy of treatment regimens and as targets for drug design.

The availability of comprehensive methods to analyze gene expression patterns for a large number of genes simultaneously has led to a flood of reports describing the expression profiles associated with an increasingly comprehensive set of biological states. The yeast, *Saccharomyces cerevisiae*, has been the subject of a majority of these reports because of the availability of the entire genomic sequence, the relatively small size of the yeast genome and the relative ease with which different experimental conditions can be tested.

The yeast system has been used to assay changes in gene expression associated with a variety of different physiological, developmental, disease and pharmacological conditions. These include: rich versus minimal media, (see, Wodicka et al., *Nat. Biotechnol.* 15:1359–1367 (1997)), progression through the mitotic cell cycle (see, Cho et al., *Mol. Cell* 2:65–73 (1998)), response to mutation (see Holstege et al., *Cell* 95:717–728 (1998)[AFFY], cellular response to DNA damage (see, Jelinsky and Sampson, *Proc. Natl. Acad. Sci. USA* 96:1486–1491 (1999)) and pseudohyphal formation under conditions of nitrogen starvation (see, Madhani et al., *Proc. Natl. Acad. Sci. USA* 96:12530–12535 (1999)) all of which are incorporated herein by reference for all purposes.

In each of these reports the approach has been to compare expression profiles from an experimental sample and a reference sample under a given set of conditions following a change in experimental conditions. Ideally a single variable is changed between the reference and experimental samples, allowing any observed changes to be attributed to the single changed variable. When an experimental sample is compared to a reference sample under less controlled circumstances the differential expression that is observed can result from either the changed experimental condition or from another difference between the two samples.

It is relatively simple to know and control many variables, such as genotype and environmental conditions such as temperature, aeration, nutrient availability, and stress conditions, when studying a model organism such as yeast in a laboratory environment. However, this approach decreases in utility as the subject increases in complexity and it becomes increasingly difficult to identify and control all variables. In a particularly preferred embodiment the subject of the present invention is human and one skilled in the art will recognize that it is difficult to identify and/or control variables when the subject is human.

Differential gene expression analysis experiments have been done in higher eukaryotes but they are typically restricted to those experiments in which variation between reference and experimental samples can be minimized. Differential gene expression experiments have been done in mice to identify variation resulting from aging and from reduced caloric intake. See, Lee et al., *Science* 285:1390–1393 (1999) which is incorporated herein by reference for all purposes. In order to limit variation not attributable to the experimental conditions, all mice used in the experiments were males of the same strain maintained under identical housing and feeding conditions.

Gene expression studies have also been done in humans to identify differences in gene expression in diseased samples. In studies of humans researchers have taken several approaches to minimize variability between experimental and reference samples. Growing cells in culture is one method that researchers have taken to model biological responses of human cells. For example, the changes in expression profiles in cultured human fibroblasts in response to human cytomegalovirus infection, have been characterized using DNA array technology. See, Zhu et al., *Proc. Natl. Acad. Sci. USA* 95: 14470–14475 (1998) which is incorporated herein by reference for all purposes. Because of the differences between in vitro cell culture and samples derived in vivo, this type of in vitro examination of gene expression is recognized by those of skill in the art to represent a highly useful but potentially distorted and incomplete picture of a normal response.

When expression profile comparisons are done using primary patient material rather than cell culture, extra steps can sometimes be taken to minimize variation resulting from unknown or uncontrolled differences between the experimental and reference samples. Typically reference and experimental samples are matched by isolating both from the same tissue type and often from the same patient in a single procedure. For example, genes that were differentially expressed in colon tumors were identified by comparing expression data from colon tumors and normal colon. See, Zhang et al., *Science* 276:1268–1272 which is incorporated herein by reference for all purposes. However, both of these approaches have limitations. If a patient has a disease that effects the entire organism or an entire organ it will not be possible to generate a normal sample from this individual. Even if an apparently normal sample can be obtained from the same individual it is possible that the sample will be affected by the disease. When a normal sample is from an individual distinct from the patient there will be differences that are attributed to differences in the physiological, pharmacological or disease states of the two individuals.

Another approach has been to compare expression profiles from a collection of samples to identify differences in gene expression between two states that consistently correlated with one state or the other in order to identify genes that could be used to predict the state of an unknown sample as being one of the two states. See Golub et al., *Science* 286:531–537 (1999) which is incorporated herein by reference for all purposes. One limitation to this approach is that only genes that consistently correlate with one state or another are useful. For example, genes that are differentially expressed only in a subset of samples would not be useful. This subset may represent samples that share another aspect of biological state such as a common physiological state.

A preferred aspect of the present invention describes a novel approach to compare expression profiles and to derive useful information about genes that are differentially expressed in response to a change in a specific variable even when it is not practical or possible to control changes in other variables. The current invention facilitates separation of differential gene expression data into physiological, disease and/or pharmacological components.

Changes in a biological system, whether the result of a disease state or normal physiological variation, will affect many constituents of a sample. In particular, as a result of regulatory, homeostatic, and/or compensatory networks and systems present in biological systems, even the direct disruption of only a single constituent can have complicated and often unpredictable effects on other constituents.

Alteration of the activity or level of a single, hypothetical protein, such as protein P is considered herein as an example. Although the activity of only protein P is directly disrupted, additional cellular constituents that are inhibited or stimulated by protein P, or which are elevated or diminished to compensate for the loss of protein P activity will also be affected. Still other cellular constituents will be affected by changes in the levels or activity of the second tier constituents, and so on.

As a further example consider a sample in which the alteration of the activity of two hypothetical proteins, P1 and P2, has been altered, the alteration of P1 resulting from a disease state and the alteration of P2 resulting from a change in physiological state. As in the first example, each alteration will affect a second tier of constituents that will, in turn, affect the levels or activity of a third tier of constituents, and so on. Measurements of the biological state of the sample will detect changes in effected constituents but will not distinguish those that result from the P1 alteration from those that result from the P2 alteration. One aspect of the current invention distinguishes between changes in the expression profile that correlate with the change in P1, resulting from the disease state, and changes that correlate with the change in P2, resulting from the change in physiological state.

Measurement of the transcriptional state of a cell is preferred in this invention because it is relatively easy to measure, it is typically more sensitive than other methods such as morphological characterization and can typically be applied more consistently than morphological characterization.

Some disease states can be difficult to identify based on morphological differences, especially at early levels of the disease state. A genetic mutation may result in a dramatic change in the expression levels of a group of genes but biological systems can compensate for changes by altering the expression of other genes. As a result of these internal compensation responses, many perturbations may have minimal effects on observable phenotypes of the system but profound effects to the composition of cellular constituents.

It will be appreciated by one skilled in the art that samples can be derived from a variety of sources including, but not limited to, single cells, a collection of cells, tissue, cell culture, urine, blood, or other bodily fluids. The tissue or cell source may include a tissue biopsy sample, a cell sorted population, cell culture, or a single cell. In a preferred embodiment, the tissue source may include brain, liver, heart, kidney, lung, spleen, retina, bone, lymph node, endocrine gland, reproductive organ, blood, nerve, vascular tissue, and olfactory epithelium. In one embodiment, eukaryotic tissue is preferred, and in another, mammalian tissue is preferred, and in yet another, human tissue is preferred.

In yet another preferred embodiment, the tissue or cell source may be embryonic or tumorigenic. Tumorigenic tissue according to the present invention may include tissue associated with malignant and pre-neoplastic conditions, not limited to the following: acute lymphocytic leukemia, acute myelocytic leukemia, myeloblastic leukemia, promyelocytic leukemia, myelomonocytic leukemia, monocytic leukemia, erythroleukemia, chronic myelocytic (granulocytic) leukemia, chronic lymphocytic leukemia, polycythemia vera, lymphoma, Hodgkin's disease, non-Hodgkin's disease, multiple myeloma, Waldenstrom's macroglobulinemia, heavy chain disease, solid tumors, endometrial cancer, ovarian cancer, leiomyoma, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma. See Fishman, et al., *Medicine,* 2d Ed. (J.B. Lippincott Co., Philadelphia, Pa. 1985) hereby incorporated by reference in its entirety for all purposes.

OVERVIEW OF THE METHODS OF THIS INVENTION

It is well understood by those of skill in the art that variation in the global pattern of gene expression underlies much of the phenotypic diversity among cells. Phenotypic diversity includes both normal variation associated with a change in physiological state and abnormal variation associated with a pharmacological or disease state. One aspect of the current invention differentiates between abnormal variation associated with disease and/or pharmacological state and normal variation associated with physiological state.

A preferred embodiment of the current invention matches an experimental sample to one or more reference samples that match the experimental sample in at least one parameter that is a determinant of physiological status, pharmacological and/or disease status and compares the expression profiles of the experimental and reference samples. In a particularly preferred embodiment, the current invention is used to identify genes that are differentially expressed between matched samples. The embodiments of the present invention are also applicable to diagnosing the disease state of a sample. The embodiments of the present invention are also applicable to characterizing and monitoring disease states. This includes identifying and monitoring the level of a disease state as well as monitoring the effect of therapies on a disease state. The embodiments of the present invention are also applicable to identifying and monitoring drug responses that are specific to a given physiological state. Thus, the present invention is also useful for designing drug therapies that are tailored to the physiological state of a subject. The present invention in one aspect can also be used to identify the physiological or pharmacological state of a sample.

Genes have been identified whose expression is varied greatly (preferably more than 4, 10, 15, or 20 fold) between different physiological states. Differences in physiological states between an experimental and reference sample make it difficult to distinguish between genes that are differentially expressed because of the change in physiological state and genes that are differentially expressed because of another difference between the samples. For example, when comparing an experimental sample to a reference sample to identify genes that are differentially expressed in a disease state, it is preferable to match the physiological state of the experimental and reference samples so that any changes in gene expression that are observed can be attributed to the disease state. Similarly, a difference in disease or pharmacological state can obscure differences in physiological state. In many embodiments the current invention matches the physiological, pharmacological and/or disease states of reference and experimental samples before comparing expression profiles.

Determining the Physiological, Pharmacological and/or Disease State of a Sample.

In one aspect the invention requires the gathering of information about the physiological, pharmacological and/or disease state of a sample. If, for example, the goal is to diagnose disease in an experimental sample from a human patient one aspect of the invention is to discover information about the physiological and pharmacological state of the sample. Another aspect of the invention is to match the experimental sample to reference samples of similar physiological and pharmacological state. This requires knowledge of the physiological and pharmacological state of the reference sample. In this example, another aspect of the invention that the reference samples are also of known disease status to allow diagnosis of the disease state of the experimental sample.

Information about physiological state can be gathered in a variety of ways. If the subject is human, the sex can be obtained for example through an interview, a visual inspection or through karyotyping.

Information about genotypic state can be derived by sequence analysis. There are a variety of methods, such as array based analysis, standard sequencing techniques, and other commercially available methods.

Information about disease state can be also be obtained through a variety of mechanisms such as identification of symptoms or morphological examination of effected tissue. Determinants of disease state include phenotypic symptoms, level of disease, progress of therapy. It is possible to have more than one disease contributing to the disease state of the sample.

Information about pharmacological state can similarly be obtained through a variety of mechanisms. In some circumstances a subject can be interviewed. Under other circumstances it may be necessary to inspect the medical history of the subject or to assay for evidence of drug use through chemical analysis of blood, urine, skin, saliva or hair.

There may be variation in the expression profiles obtained from samples that apparently share a common physiological state. In some embodiments of the invention the best expression profile to use as a reference sample is an average from a plurality of expression profiles of common physiological state. A phenotypic disease state may alter physiological state expression profile (women with a history of sexual abuse have dramatically altered levels of certain hormones-this would be a disease state that might go clinically undetected).

Matching Reference Sample(s) to Experimental Sample(s).

According to one aspect of the current invention, samples can be matched by disease state, by physiological state, or by pharmacological state, or any combination of these states. The objective is to minimize differences between the experimental and reference samples. In a particularly preferred embodiment variation between the experimental and reference sample is limited to a single aspect of a disease, physiological or pharmacological state that is being interrogated. In another embodiment the invention removes variation due to one or more indicators of physiological status, pharmacological status or disease status.

In another aspect the invention removes variation due to one or more indicators of physiological status and one or more indicators of pharmacological status. In another aspect the invention removes variation due to one or more indicators of physiological status and one or more indicators of disease status. In another aspect the invention removes variation due to one or more indicators of disease status and one or more indicators of pharmacological status.

In one aspect of the invention the reference sample(s) is selected to match the experimental sample in at least one parameter that is a determinant of physiological state. In this aspect of the invention it is preferable that the reference sample(s) matches the experimental sample in many parameters that are determinants of physiological state. The reference sample and the experimental sample could be from subjects that are similar in age, gender, reproductive status or ethnic origin, any combination of these aspects or other aspects that are determinants of physiological state.

In one aspect of the invention the reference sample is selected to match the experimental sample in at least one aspect of a disease state. In this aspect of the invention it is preferable that the reference sample(s) matches the experimental sample in many parameters that are determinants of disease state.

In another aspect of the invention the reference sample is selected to match the experimental sample in at least one aspect of a pharmacological state. In this aspect of the invention it is preferable that the reference sample(s) matches the experimental sample in many parameters that are determinants of pharmacological state.

Identifying Differentially Expressed Genes from Matched Samples.

In one embodiment of the invention matched experimental and reference samples are compared to identify differences. Comparisons that can be made include, but are not limited to: diseased to normal from matching physiological state, diseased to diseased from different physiological states, normal to normal from different physiological states, diseased to diseased from the same physiological state, and normal to normal from the same physiological state. A sample of unknown physiological state can be compared to a plurality of samples of known physiological state to identify the physiological state of the sample.

In many embodiments of the current invention, expression profiles will be compared. In a particularly preferred embodiment expression profiles are compared to identify genes that are differentially expressed between the samples. This embodiment of the invention is useful, for example, for identifying genes that are differentially expressed in a diseased and normal sample or in different levels of disease. Genes that are differentially expressed can be used as diagnostic or prognostic markers or drug/therapy targets or indicators of physiological or pharmacological status. They can be used individually or in sets of, for example, 2, 5, 10, 20, 30, 100, 150, 200, 250, 500, or 1,000 or more. The identified genes can be used to design probes for microarrays.

Diagnosing Disease States.

In a particularly preferred embodiment the current invention can be used to diagnose disease. Reference samples are selected to match the experimental sample in physiological and/or pharmacological state and to represent a plurality of different known disease states. The expression profile from the experimental sample is then compared to a plurality of expression profiles from reference samples to identify one or more reference samples that match the expression profile of the experimental sample. The experimental sample is diagnosed with the disease of the matching reference sample(s).

In one aspect of the invention the disease states represented are selected from a subset of diseases that match one or more symptoms in the experimental sample. For example, if the experimental sample is from a 30-year-old female patient with difficulty becoming pregnant, samples from 30-year-old females diagnosed with specific forms of infertility can be chosen as reference samples.

Monitoring Disease States.

Following the diagnosis of a particular disease in a patient or subject it is often useful to obtain information about the level of the disease state. If diagnosis is followed by therapy it is also often useful to obtain information about the level of the disease state during and after therapy.

In one aspect the invention is used to identify or characterize the stage of a tumor. Tumorogenic experimental samples are compared to reference samples that are matched to the experimental sample in one or more indicators of physiological or pharmacological status. Reference samples with well characterized tumors are selected. Comparison can be of morphological features or of other biological readouts including expression profiles. The present method stages tumors by comparison to reference samples of matching physiological and/or pharmacological state, thus eliminating gene expression differences that result from differences in physiological and/or pharmacological state that may not be relevant to the disease state.

In one embodiment the present invention can be used for monitoring the disease state of a subject undergoing one or more therapies. This requires the comparison of a sample before treatment with samples following treatment. There may be changes to the physiological state of the patient that occur over the course of the therapy that are unrelated to the therapy. When comparing a sample before treatment to a sample after treatment it will be preferable to identify changes between the samples that result from a change in physiological state. In one aspect the current invention identifies changes that are the result of physiological change rather than therapeutic intervention.

Identifying and Monitoring Drug Responses that are Specific to Physiological State.

The current invention can be used to correlate differences in drug efficacy with differences in physiological state. Some drug therapies are highly effective in one patient but ineffective or deleterious in another patient. Differences in drug efficacy may correlate with differences in genotypic state, disease state or physiological state.

The current invention can be used to identify changes in gene expression following drug treatment that are specific to a physiological state. This could facilitate the discovery/design of therapies that are specific for the physiological state of the patient.

Drug therapies will have different effects depending on the physiological status of subject. Some drug therapies have different side effects in different physiological states. Some drug therapies have different efficacies in men and women; in particular many are less effective in women than in men. In a preferred embodiment the current invention is used to identify drug effects that are specific to women. In another preferred embodiment the method is used to identify drug effects that are specific to men.

The invention can also be used to identify therapeutic regimens that are optimized for the physiological state of the patient. Therapeutic treatments ideally impart maximal disease reduction with minimal adverse side effects, but many therapeutic treatments do have undesirable side effects. These side effects may be specific to the physiological state of the sample. The current invention could be used as a tool to design therapeutic regimens that are specific for the physiological state of the subject.

Identifying the Physiological State of an Experimental Sample.

A sample for which relatively little information is known about the subject from which the sample was supplied could be compared to a plurality of expression profiles of known physiological status in order to determine the physiological status of the subject. For example a blood or semen sample isolated from a crime scene could be used to obtain information about the physiological status of the criminal, such as age and ethnic origin.

Specific Applications

Those skilled in the art will recognize that in a preferred embodiment, the expression profiles from the reference samples will be input to a database. A relational database is preferred and can be used, but one of skill in the art will recognize that other databases could be used. A relational database is a set of tables containing data fitted into predefined categories. Each table, or relation, contains one or more data categories in columns. Each row contains a unique instance of data for the categories defined by the columns. For example, a typical database for the invention would include a table that describes a sample with columns for age, gender, reproductive status, expression profile and so forth. Another table would describe a disease: symptoms, level, sample identification, expression profile and so forth. See U.S. Ser. No. 09/354,935, which is hereby incorporated by reference in its entirety for all purposes.

In one embodiment the invention matches the experimental sample to a database of reference samples. The database is assembled with a plurality of different samples to be used as reference samples. An individual reference sample in one embodiment will be obtained from a patient during a visit to a medical professional. The sample could be for example a tissue, blood, urine, feces or saliva sample. Information about the physiological, disease and/or pharmacological status of the sample will also be obtained through any method available. This may include, but is not limited to, expression profile analysis, clinical analysis, medical history and/or patient interview. For example, the patient could be interviewed to determine age, sex, ethnic origin, symptoms or past diagnosis of disease, and the identity of any therapies the patient is currently undergoing. A plurality of these reference samples will be taken. A single individual may contribute a single reference sample or more than one sample over time. One skilled in the art will recognize that confidence levels in predictions based on comparison to a database increase as the number of reference samples in the database increases. One skilled in the art will also recognize that some of the indicators of status will be determined by less precise means, for example information obtained from a patient interview is limited by the subjective interpretation of the patient. Additionally, a patient may lie about age or lack sufficient information to provide accurate information about ethnic or other information. Descriptions of the severity of disease symptoms is a particularly subjective and unreliable indicator of disease status.

The database is organized into groups of reference samples. Each reference sample contains information about physiological, pharmacological and/or disease status. In one aspect the database is a relational database with data organized in three data tables, one where the samples are grouped primarily by physiological status, one where the samples are grouped primarily by disease status and one where the samples are grouped primarily by pharmacological status. Within each table the samples can be further grouped according to the two remaining categories. For example the physiological status table could be further categorized according to disease and pharmacological status.

As will be appreciated by one of skill in the art, the present invention may be embodied as a method, data processing system or program products. Examples of computer programs and databases are shown in U.S. Ser. Nos. 09/354,935, 08/828,952, 09/341,302, 09/397,494, 60/220,587, and 60/220,645, which are hereby incorporated by reference in their entireties for all purposes.

Accordingly, the present invention may take the form of data analysis systems, methods, analysis software and etc. Software written according to the present invention is to be stored in some form of computer readable medium, such as memory, hard-drive, DVD ROM or CD ROM, or transmitted over a network, and executed by a processor. The present invention also provides a computer system for analyzing physiological states, levels of disease states and/or therapeutic efficacy. The computer system comprises a processor, and memory coupled to said processor which encodes one or more programs. The programs encoded in memory cause the processor to perform the steps of the above methods wherein the expression profiles and information about physiological, pharmacological and disease states are received by the computer system as input.

U.S. Pat. No. 5,733,729 illustrates an example of a computer system that may be used to execute the software of an embodiment of the invention. This patent shows a computer system that includes a display, screen, cabinet, keyboard, and mouse. The mouse may have one or more buttons for interacting with a graphic user interface. The cabinet preferably houses a CD-ROM or DVD-ROM drive, system memory and a hard drive which may be utilized to store and retrieve software programs incorporating computer code that implements the invention, data for use with the invention and the like. Although a CD is shown as an exemplary computer readable medium, other computer readable storage media including floppy disk, tape, flash memory, system memory, and hard drive may be utilized.

Additionally, a data signal embodied in a carrier wave (e.g., in a network including the internet) may be the computer readable storage medium.

The patent also shows a system block diagram of a computer system used to execute the software of an embodiment of the invention. The computer system includes monitor, and keyboard, and mouse. The computer system further includes subsystems such as a central processor, system memory, fixed storage (e.g., hard drive), removable storage (e.g., CD-ROM), display adapter, sound card, speakers, and network interface. Other computer systems suitable for use with the invention may include additional or fewer subsystems. For example, another computer system may include more than one processor or a cache memory. Computer systems suitable for use with the invention may also be embedded in a measurement instrument. The embedded systems may control the operation of, for example, a GeneChip® Probe array scanner as well as executing computer codes of the invention.

Computer methods can be used to measure the variables and to match samples to eliminate gene expression differences that are a result of differences that are not of interest. For example, a plurality of values can be input into computer code for one or more of a: physiological, pharmacological or disease states. The computer code can thereafter measure the differences or similarities between the values to eliminate changes not attributable to a value of interest. Examples of computer programs and databases that can be used for this purpose are shown U.S. Ser. Nos. 09/354,935, 08/828,952, 09/341,302, 09/397,494, 60/220,587, and 60/220,645, which are hereby incorporated by reference in their entireties.

In one aspect of the invention, microarrays will be used to measure expression profiles. Microarrays are particularly well suited because of the reproducibility between different experiments. DNA microarrays provide one method for the simultaneous measurement of the expression levels of large numbers of genes. Each array consists of a reproducible pattern of thousands of different DNAs attached to a solid support. Labeled RNA or DNA is hybridized to complementary probes on the array and then deteced by laser scanning. Hybridization intensities for each probe on the array are determined and converted to a quantitative read-out of relative gene expression levels. The data can be further analyzed to identify expression patterns and variation that correlates with the biological state of the sample. (See U.S. Pat. Nos. 6,040,138, 5,800,992 and 6,020,135, 6,033,860 and U.S. Ser. No. 09/341,302 which are incorporated herein by reference.)

High-density oligonucleotide arrays are particularly useful for monitoring the gene expression pattern of a sample. In one approach, total mRNA isolated from the sample is converted to labeled cRNA and then hybridized to an array such as a GeneChip® oligonucleotide array. Each sample is hybridized to a separate array. Relative transcript levels are calculated by reference to appropriate controls present on the array and in the sample. See Mahadevappa, M. & Warrington, J. A. *Nat. Biotechnol.* 17, 1134–1136 (1999) which is hereby incorporated by reference in its entirety for all purposes.

Characterization of Biological Status in Females.

The current invention is particularly useful when applied to analysis of experimental samples from female subjects. Women differ from men in the physiological indicator of gender, which contributes to an as yet uncharacterized level of differential gene expression. In addition, there is a tremendous amount of normal variation between female subjects and between different samples from the same female subject. In particular, the female reproductive system and the menstrual cycle add an additional level of physiological variation to the analysis of samples derived from female subjects. As part of a monthly cycle the lining of the female uterus, the endometrium, undergoes a cycle of controlled tissue remodeling unparalleled in other organs. This cycle is presumably driven by changes in gene expression.

Physiological variation between women and men complicates the design of effective therapies for women and the monitoring of therapeutic treatments in women. It is currently well accepted that gender differences result in extensive disparity in the ways males and females respond to therapeutic treatments for a variety of non-gender specific diseases including heart disease and stroke. The reasons for these differences, however, are not well understood, but the menstrual cycle is likely to be at least partially responsible. Much of the research into novel drugs and therapeutic treatments is done using male test subjects. Therefore, there is a great need in the art for methods of incorporating information about the physiological state of a patient into the diagnosis and management of diseases.

Gender differences in the efficacy of drug therapy have been appreciated for many years, but little has been done to investigate these differences. It is believed that hormonal fluctuations within the menstrual cycle may be a primary cause of gender specific drug response. A systematic investigation of the physiological variation throughout the menstrual cycle, both under normal physiological conditions and in response to drug treatment, would be beneficial.

In one embodiment, the current invention correlates information about variation in gene expression with variation in gender. Male and female samples that are matched in other indicators of physiological state are compared to identify genes that are differentially expressed. For example a healthy 30-year-old male of similar, i.e., European, descent could be compared to a healthy 30-year-old female of European descent to identify genes that are differentially expressed between the two physiological conditions. In a further embodiment the current invention could also be used to monitor changes in pharmacological status resulting from drug treatments, taking normal physiological variation into account. For example, the subjects in the first example could be compared again following therapeutic treatment. The genes that were identified in the first example would be compared or subtracted from the genes identified in the second example to identify genes that are differentially expressed as a result of the therapy.

In another aspect, the current invention diagnoses diseases of the female reproductive system. Many disorders of the female reproductive system have relatively poor methods of diagnosis and prognosis and many are typically diagnosed based simply on patient perception, which tends to be unreliable. For example, pre-menstrual syndrome effects large numbers of women, but is typically diagnosed only when other explanations for the observed symptoms are eliminated. More reliable methods of diagnosis such as the use of gene expression profiles for diagnosis and prognosis have been complicated by the changes in gene expression that accompany the normal physiological variation of the system.

Menopause is a woman's final menstrual period, but currently the actual event can be determined only in retrospect, after she has not had a period for 12 continuous months. Menopause can occur naturally any time between the mid-30s through the late 50s, but can also be brought on prematurely by events such as gynecological surgery, cancer therapy and certain illnesses and diseases. The current invention can be used to determine a molecular profile consistent with a diagnosis of menopause that would allow earlier diagnosis.

In one embodiment the current invention diagnosis diseases of the female reproductive organs. An expression profile from an experimental sample is compared to expression profiles from reference samples that match the experimental sample in physiological state. The reference samples represent a plurality of different disease states that effect the uterus and the experimental sample is identified as being of the disease state of the reference sample that is the closest match. The samples can be derived from, for example, endometrial tissue, myometrial tissue, and/or uterine tissue.

In one aspect, a database of reference samples could be comprised of expression profiles from endometrial samples and data points identifying the physiological, pharmacological and/or disease state of the samples. These reference samples would be from many different individuals representing many different physiological, pharmacological and/or disease states. The reference samples can be derived from for example: normal tissue at different stages of development and differentiation, tissues affected with a variety of pathological conditions, including but not limited to, pre-menstrual syndrome, PMDD, stress urinary incontinence, polycystic ovarian disease, endometriosis, endometrial cancer, infertility, hormone imbalance, and tissue subjected to a variety of perturbations including but not limited to hormone replacement therapy, or chemical contraception. In one preferred embodiment, reference samples will be taken from individuals during routine doctor visits. In one embodiment the reference samples would represent different physiological states of the menstrual cycle including but not limited to the secretory and proliferative stages of the endometrium.

Providing a Nucleic Acid Sample.

One of skill in the art will appreciate that it is desirable to have nucleic samples containing target nucleic acid sequences that reflect the transcripts of interest. Therefore, suitable nucleic acid samples may contain transcripts of interest. Suitable nucleic acid samples, however, may contain nucleic acids derived from the transcripts of interest. As used herein, a nucleic acid derived from a transcript refers to a nucleic acid for whose synthesis the mRNA transcript or a subsequence thereof has ultimately served as a template. Thus, a cDNA reverse transcribed from a transcript, an RNA transcribed from that cDNA, a DNA amplified from the cDNA, an RNA transcribed from the amplified DNA, etc., are all derived from the transcript and detection of such derived products is indicative of the presence and/or abundance of the original transcript in a sample. Thus, suitable samples include, but are not limited to, transcripts of the gene or genes, cDNA reverse transcribed from the transcript, cRNA transcribed from the cDNA, DNA amplified from the genes, RNA transcribed from amplified DNA, and the like.

Transcripts, as used herein, may include, but not limited to pre-mRNA nascent transcript(s), transcript processing intermediates, mature mRNA(s) and degradation products. It is not necessary to monitor all types of transcripts to practice this invention. For example, one may choose to practice the invention to measure the mature MRNA levels only.

In one embodiment, such sample is a homogenate of cells or tissues or other biological samples. Preferably, such sample is a total RNA preparation of a biological sample. More preferably in some embodiments, such a nucleic acid sample is the total mRNA isolated from a biological sample. Those of skill in the art will appreciate that the total MRNA prepared with most methods includes not only the mature MRNA, but also the RNA processing intermediates and nascent pre-mRNA transcripts. For example, total MRNA purified with poly (T) column contains RNA molecules with poly (A) tails. Those poly A+ RNA molecules could be mature mRNA, RNA processing intermediates, nascent transcripts or degradation intermediates.

Biological samples may be of any biological tissue or fluid or cells. Frequently the sample will be a "clinical sample" which is a sample derived from a patient. Clinical samples provide rich sources of information regarding the various states of genetic network or gene expression. Some embodiments of the invention are employed to detect mutations and to identify the function of mutations. Such embodiments have extensive applications in clinical diagnostics and clinical studies. Typical clinical samples include, but are not limited to, sputum, blood, blood cells (e.g., white cells), tissue or fine needle biopsy samples, urine, peritoneal fluid, and pleural fluid, or cells therefrom. Biological samples may also include sections of tissues such as frozen sections taken for histological purposes.

Another typical source of biological samples are cell cultures where gene expression states can be manipulated to explore the relationship among genes. In one aspect of the invention, methods are provided to generate biological samples reflecting a wide variety of states of the genetic network.

One of skill in the art would appreciate that it is desirable to inhibit or destroy RNase present in homogenates before homogenates can be used for hybridization. Methods of inhibiting or destroying nucleases are well known in the art. In some preferred embodiments, cells or tissues are homogenized in the presence of chaotropic agents to inhibit nuclease. In some other embodiments, RNases are inhibited or destroyed by heat treatment followed by proteinase treatment.

Methods of isolating total mRNA are also well known to those of skill in the art. For example, methods of isolation and purification of nucleic acids are described in detail in Chapter 3 of Laboratory Techniques in Biochemistry and Molecular Biology: Hybridization With Nucleic Acid Probes, Part I. Theory and Nucleic Acid Preparation, P. Tijssen, ed. Elsevier, N.Y. (1993) and Chapter 3 of Laboratory Techniques in Biochemistry and Molecular Biology: Hybridization With Nucleic Acid Probes, Part I. Theory and Nucleic Acid Preparation, P. Tijssen, ed. Elsevier, N.Y. (1993)).

In a preferred embodiment, the total RNA is isolated from a given sample using, for example, an acid guanidinium-phenol-chloroform extraction method and polyA$^+$ mRNA is isolated by oligo dT column chromatography or by using (dT)n magnetic beads (see, e.g., Sambrook et al., Molecular Cloning: A Laboratory Manual (2nd ed.), Vols. 1–3, Cold Spring Harbor Laboratory, (1989), or Current Protocols in Molecular Biology, F. Ausubel et al., ed. Greene Publishing and Wiley-Interscience, New York (1987)). See also PCT/US99/25200 for complexity management and other sample preparation techniques, which is hereby incorporated by reference in its entirety.

Frequently, it is desirable to amplify the nucleic acid sample prior to hybridization. One of skill in the art will appreciate that whatever amplification method is used, if a quantitative result is desired, care must be taken to use a method that maintains or controls for the relative frequencies of the amplified nucleic acids to achieve quantitative amplification.

Methods of "quantitative" amplification are well known to those of skill in the art. For example, quantitative PCR involves simultaneously co-amplifying a known quantity of a control sequence using the same primers. This provides an internal standard that may be used to calibrate the PCR reaction. The high density array may then include probes specific to the internal standard for quantification of the amplified nucleic acid.

Other suitable amplification methods include, but are not limited to polymerase chain reaction (PCR) (Innis, et al., PCR Protocols. A guide to Methods and Application. Academic Press, Inc. San Diego, (1990)), ligase chain reaction (LCR) (see Wu and Wallace, Genomics, 4: 560 (1989), Landegren, et al., Science, 241: 1077 (1988) and Barringer, et al., Gene, 89: 117 (1990), transcription amplification (Kwoh, et al., Proc. Natl. Acad. Sci. USA, 86: 1173 (1989)), and self-sustained sequence replication (Guatelli, et al., Proc. Nat. Acad. Sci. USA, 87: 1874 (1990)).

Cell lysates or tissue homogenates often contain a number of inhibitors of polymerase activity. Therefore, RT-PCR typically incorporates preliminary steps to isolate total RNA or mRNA for subsequent use as an amplification template. One tube mRNA capture methods may be used to prepare poly(A)+ RNA samples suitable for immediate RT-PCR in the same tube (Boehringer Mannheim). The captured mRNA can be directly subjected to RT-PCR by adding a reverse transcription mix and, subsequently, a PCR mix. In a particularly preferred embodiment, the sample mRNA is reverse transcribed with a reverse transcriptase and a primer consisting of oligo dT and a sequence encoding the phage T7 promoter to provide single stranded DNA template. The second DNA strand is polymerized using a DNA polymerase. After synthesis of double-stranded cDNA, T7 RNA polymerase is added and RNA is transcribed from the cDNA template. Successive rounds of transcription from each single cDNA template result in amplified RNA. Methods of in vitro polymerization are well known to those of skill in the art (see, e.g., Sambrook, supra).

It will be appreciated by one of skill in the art that the direct transcription method described above provides an antisense (aRNA) pool. Where antisense RNA is used as the target nucleic acid, the oligonucleotide probes provided in the array are chosen to be complementary to subsequences of the antisense nucleic acids. Conversely, where the target nucleic acid pool is a pool of sense nucleic acids, the oligonucleotide probes are selected to be complementary to subsequences of the sense nucleic acids. Finally, where the nucleic acid pool is double stranded, the probes may be of either sense as the target nucleic acids include both sense and antisense strands.

The protocols cited above include methods of generating pools of either sense or antisense nucleic acids. Indeed, one approach can be used to generate either sense or antisense nucleic acids as desired. For example, the cDNA can be directionally cloned into a vector (e.g., Stratagene's p Bluscript II KS (+) phagemid) such that it is flanked by the T3 and T7 promoters. In vitro transcription with the T3 polymerase will produce RNA of one sense (the sense depending on the orientation of the insert), while in vitro transcription with the T7 polymerase will produce RNA having the opposite sense. Other suitable cloning systems include phage lambda vectors designed for Cre-loxP plasmid subcloning (see e.g., Palazzolo et al., Gene, 88: 25–36 (1990)).

Other analysis methods that can be used in the present invention include electrochemical denaturation of double stranded nucleic acids, U.S. Pat. Nos. 6,045,996 and 6,033,850, the use of multiple arrays (arrays of arrays), U.S. Pat. No. 5,874,219, the use of scanners to read the arrays, U.S. Pat. Nos. 5,631,734; 5,744,305; 5,981,956 and 6,025,601, methods for mixing fluids, U.S. Pat. No. 6,050,719, integrated device for reactions, U.S. Pat. No. 6,043,080, integrated nucleic acid diagnostic device, U.S. Pat. No. 5,922,591, and nucleic acid affinity columns, U.S. Pat. No. 6,013,440. All of the above patents are hereby incorporated by reference in their entireties.

Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

All publications and patent applications cited above are incorporated by reference in their entirety for all purposes to the same extent as if each individual publication or patent application were specifically and individually indicated to be so incorporated by reference. Although the present invention has been described in some detail by way of illustration and example for purposes of clarity and understanding, it will be apparent that certain changes and modifications may be practiced within the scope of the appended claims.

The above disclosure generally describes the present invention. A more complete understanding can be obtained by reference to the following specific examples which are provided herein for purposes of illustration only, and are not intended to limit the scope of the invention.

EXAMPLES

The following examples are offered to illustrate, but not to limit the present invention.

Example 1

Detection of genes differentially expressed in the secretory and proliferative stage endometrium. This is the first report of differential expression between two different physiological states in human subjects. The data obtained from this experiment demonstrates that there are differences in gene expression between different physiological states in humans. These differences are large enough to be detected by arrays and the number of genes changed is substantial but manageable, making the information useful for diagnostic and prognostic applications.

Experiments were designed to identify genes that were differentially expressed in the physiologically distinct secretory and proliferative stages of endometrial tissue. Gene expression levels were quantitatively measured in tissue samples using high density oligonucleotide arrays containing probes representing approximately 6800 full-length human genes (commercially available from Affymetrix, Santa Clara). Probe arrays (DNA chips) of this type have been shown to behave quantitatively with high specificity and sensitivity (Lockhart, D. J. et al., 1996, Nat. Biotech. 14:1657–1680). See also, U.S. Pat. No. 6,040,138. The probe sequences were based on information from public sequence databases, such a GenBank. Samples derived from secretory and proliferative stage endometrium were hybridized to the probe arrays and the relative concentration of more than 6800 human genes were measured simultaneously. The RNAs were classified by relative abundance and differentially expressed genes were identified by direct comparison. Using this method one can produce, in a relatively short period of time, a quantitative representation of gene expression for a plurality of different physiological states for a plurality of different cell or tissue types.

TABLE 1

Genes downregulated in proliferative vs. secretory endometrium

| Probe Set | Avg Diff Change | Fold Change | Entrez Definition |
|---|---|---|---|
| HG721-HT4828 | −13342 | −56.6 | Placental Protein 14, Endometrial Alpha 2 Globulin, Alt. Splice 3 |
| HG721-HT4827 | −12704 | −45.5 | Placental Protein 14, Endometrial Alpha 2 Globulin, Alt. Splice 2 |
| D00632 | −8069 | −27.7 | Human plasma (extracellular) mRNA for glutathione peroxidase, complete cds |
| X64177 | −11610 | −39.3 | H. sapiens mRNA for metallothionein |
| X04470 | −6159 | −16.8 | Human mRNA for antileukoprotease (ALP) from cervix uterus |
| M83667 | −5851 | −14.9 | Human NF-IL6-beta protein mRNA, complete cds |
| M13690 | −5998 | −13.8 | Human plasma protease (C1) inhibitor mRNA, complete cds |
| Y10032 | −3126 | −13.4 | H. sapiens mRNA for putative serine/threonine protein kinase |
| X65965 | −1760 | −11.1 | H. sapiens SOD-2 gene for manganese superoxide dismutase |
| M34455 | −3551 | −8.6 | Human interferon-gamma-inducible indoleamine 2,3-dioxygenase (IDO) mRNA, complete cds |
| U10117 | −1315 | −10.8 | Human endothelial-monocyte activating polypeptide II mRNA, complete cds |
| D15050 | −668 | −5 | Human mRNA for transcription factor AREB6, complete cds |
| K02765_at | −8578 | −8.1 | Human complement component C3 mRNA, alpha and beta subunits, complete cds |
| M59815 | −6015 | −7.3 | Human complement component C4A gene |
| J02611 | −10627 | −8.8 | Human apolipoprotein D mRNA, complete cds |
| M60974 | −977 | −5.2 | Human growth arrest and DNA-damage-inducible protein (gadd45) mRNA, complete cds |
| U28368 | −1357 | −6.7 | Human Id-related helix-loop-helix protein Id4 mRNA, complete cds |
| M85276 | −10891 | −14.3 | Homo sapiens NKG5 gene, complete cds |
| HG2981-HT3127 | −722 | −7.1 | Epican, Alt. Splice 11 |
| X92744 | −3311 | −10.6 | H. sapiens mRNA for hBD-1 protein |
| X97324 | −1020 | −7.4 | H. sapiens mRNA for adipophilin./gb = X97324/ntype = RNA |
| M55153 | −2002 | −6.5 | Human transglutaminase (TGase) mRNA, complete cds |
| M61916 | −1907 | −5.8 | Human laminin B1 chain mRNA, complete cds |
| M55543 | −370 | *−4.3 | Human guanylate binding protein isoform II (GBP-2) mRNA, complete cds |
| M97796 | −3808 | −5.4 | Human helix-loop-helix protein (Id-2) mRNA, complete cds |
| M13929 | −1042 | −5.6 | Human c-myc-P64 mRNA, initiating from promoter P0, (HLmyc2.5) partial cds |
| L00058 | −886 | −5.5 | Human (GH) germline c-myc proto-oncogene, 5′ flank |
| U02556 | −3709 | −9.2 | Human RP3 mRNA, complete cds |
| J04080 | −8872 | −6.2 | Human complement component C1r mRNA, complete cds |
| U08989 | −984 | −6.4 | Human glutamate transporter mRNA, complete cds |
| X16396 | −615 | −5.9 | Human mRNA for NAD-dependent methylene tetrahydrofolate dehydrogenase cyclohydrolase (EC 1.5.1.15) |

TABLE 1-continued

Genes downregulated in proliferative vs. secretory endometrium

| Probe Set | Avg Diff Change | Fold Change | Entrez Definition |
|---|---|---|---|
| M26062 | −1378 | −11.6 | Human interleukin 2 receptor beta chain (p70–75) mRNA, complete cds |
| U63455 | −1401 | −6.3 | Human sulfonylurea receptor (SUR1) gene |
| X69699 | −4265 | −5.4 | H. sapiens Pax8 mRNA |
| M24069 | −1090 | −6.1 | Human DNA-binding protein A (dbpA) gene, 3' end |
| M27492 | −2004 | −4.6 | Human interleukin 1 receptor mRNA, complete cds |
| M14058 | −4723 | −5.4 | Human complement C1r mRNA, complete cds |
| S37730 | −6004 | −6.9 | insulin-like growth factor binding protein-2 [human, placenta, Genomic, 4575 nt 4 segments] |
| U46499 | −1951 | −4.5 | Human microsomal glutathione transferase (GST12) gene, 5' sequence |
| M21574 | −2474 | −6 | Human platelet-derived growth factor receptor alpha (PDGFRA) mRNA, complete cds |
| U65093 | −1037 | −6.9 | Human msg1-related gene 1 (mrg1) mRNA, complete cds |
| X76717 | −5904 | −8.5 | H. sapiens MT-11 mRNA |
| U33147 | −976 | −7.5 | Human mammaglobin mRNA, complete cds |
| U09284 | −1158 | −4.5 | Human PINCH protein mRNA, complete cds |
| M94856 | −1105 | −4.9 | Human fatty acid binding protein homologue (PA-FABP) mRNA, complete cds |
| X65614 | −5954 | −28.9 | H. sapiens mRNA for calcium-binding protein S100P |
| Z68228 | −2909 | −5 | H. sapiens mRNA for plakoglobin |
| D87953 | −2386 | −4.4 | Human mRNA for RTP, complete cds |
| K02574 | −1199 | −4 | Human purine nucleoside phosphorylase (PNP) mRNA, complete cds |
| X05908 | −744 | −4.4 | Human mRNA for lipocortin |
| U21936 | −1382 | *−13.4 | Human peptide transporter (HPEPT1) mRNA, complete cds |
| J04102 | −689 | *−7.2 | Human erythroblastosis virus oncogene homolog 2 (ets-2) mRNA, complete cds |
| M62486 | −1190 | *−11.7 | Human C4b-binding protein gene |
| Z19002 | −1444 | *−14.0 | H. sapiens of PLZF gene encoding kruppel-like zinc finger protein |
| X57348 | −1411 | *−13.7 | H. sapiens mRNA (clone 9112) |
| M15958 | −1554 | *−15.0 | Human gastrin gene, complete cds |
| M13955 | −363 | *−4.3 | Human mesothelial keratin K7 (type II) mRNA, 3' end |
| U51010 | −1007 | *−10.1 | Human nicotinamide N-methyl-transferase gene, exon 1 and 5' flanking region./gb = U51010/ntype = DNA/annot = exon |
| M92357 | −1377 | −11.6 | Homo sapiens B94 protein mRNA, complete cds |
| M38591 | −1176 | *−11.6 | Homo sapiens cellular ligand of annexin II (p11) mRNA, complete cds |
| U20758 | −1314 | *−12.8 | Human osteopontin gene, complete cds |
| M13699 | −2125 | *−20.1 | Human ceruloplasmin (ferroxidase) mRNA, complete cds |
| J05068 | −1459 | *−14.1 | human transcobalamin I mRNA, complete cds |
| L32137 | −1246 | *−12.2 | Human germline oligomeric matrix protein (COMP) mRNA, complete cds |
| U08021 | −2064 | *−19.6 | Human nicotinamide N-methyl-transferase (NNMT) mRNA, complete cds |
| U07919 | −3912 | *−36.2 | Human aldehyde dehydrogenase 6 mRNA, complete cds |
| M84526 | −3742 | *−34.7 | Human adipsin/complement factor D mRNA, complete cds |
| X96719 | −388 | *−4.5 | H. sapiens mRNA for AICL (activation-induced C-type lectin) |
| L09235 | −895 | *−9.0 | Human vacuolar ATPase (isoform VA68) mRNA, complete cds |
| U14528 | −499 | *−5.5 | Human sulfate transporter (DTD) mRNA, complete cds |
| HG4321–HT4591 | −336 | *−4.0 | Ahnak-Related Sequence |
| X95240 | −591 | *−6.3 | H. sapiens mRNA for cysteine-rich secretory protein-3 |
| X58079 | −388 | *−4.5 | Human mRNA for S100 alpha protein |
| U42031 | −696 | *−7.3 | Human 54 kDa progesterone receptor-associated immunophilin FKBP54 mRNA, partial cds |
| M31516 | −841 | *−8.6 | Human decay-accelerating factor mRNA, complete cds |
| X92814 | −669 | *−7.0 | H. sapiens mRNA for rat HREV107-like protein |
| X87342 | −581 | *−6.2 | H. sapiens mRNA for human giant larvae homolog |
| U60873 | −388 | *−4.5 | Human clone 137308 mRNA, partial cds |
| U00115 | −622 | *−6.6 | Human zinc-finger protein (bcl-6) mRNA, complete cds |
| L11005 | −422 | *−4.8 | Human aldehyde oxidase (hAOX) mRNA, complete cds |
| Z26653 | −1126 | *−11.1 | H. sapiens mRNA for laminin M chain (merosin) |
| D31762 | −739 | *−7.6 | Human mRNA for KIAA0057 gene, complete cds |
| U25997 | −728 | *−7.5 | Human stanniocalcin precursor (STC) mRNA, complete cds |
| U17760 | −700 | *−7.3 | Human laminin S B3 chain (LAMB3) gene |
| U26173 | −615 | *−6.5 | Human bZIP protein NF-IL3A (IL3BP1) mRNA, complete cds |
| M57730 | −827 | *−8.4 | Human B61 mRNA, complete cds |
| M22430 | −1069 | *−10.6 | Human RASF-A PLA2 mRNA, complete cds |
| V00594 | −15429 | *−139.7 | Human mRNA for metallothionein from cadmium-treated cells |

*expression level in proliferative was close to 0. Indistinguishable from background.

TABLE 2

Genes upregulated in proliferative vs. secretory

| Accession number | Avg Diff Change | Fold Change | Entrez Definition |
|---|---|---|---|
| M34516 | 4759 | *43.8 | Human omega light chain protein 14.1 (Ig lambda chain related) gene |
| M63438 | 8960 | *81.6 | Human Ig rearranged gamma chain mRNA, V-J-C region and complete cds |
| L22524 | 717 | *7.4 | Human matrilysin mRNA |
| X57766 | 6160 | 7 | Human stromelysin-3 mRNA |
| M16364 | 1877 | *17.9 | Human creatine kinase-B mRNA, complete cds |
| M68516 | 910 | 6.7 | PCI gene (plasminogen activator inhibitor 3) extracted from Human protein C inhibitor gene, complete cds |
| J04970 | 998 | *10.0 | Human carboxypeptidase M, 3' end |
| U83411 | 1586 | *15.3 | Homo sapiens carboxypeptidase Z precursor, mRNA, complete cds. |
| U79299 | 1359 | 6 | Human neuronal olfactomedin-related ER localized protein mRNA, partial cds. |
| L38517 | 1527 | *14.7 | Homo sapiens indian hedgehog protein (IHH) mRNA, 5' end |
| M96789 | 914 | *9.2 | Homo sapiens connexin 37 (GJA4) mRNA, complete cds |

TABLE 2-continued

Genes upregulated in proliferative vs. secretory

| Accession number | Avg Diff Change | Fold Change | Entrez Definition |
|---|---|---|---|
| AFFX-HUMRGE/ M10098_M_at | 6662 | 16.2 | |
| AFFX-HUMRGE/ M10098_5_at | 3192 | 13.7 | |

*expression level in secretory was close to 0. Indistinguishable from background.

Example 2

Detection of gene expression changes in endometrial cancer (adenocarcinoma and clear cell carcinoma). The goals of the experiment were an improved understanding of etiology, identification of candidate genes, improved diagnostics, and improved therapeutics. Tissues used in the study were 4 matched adenocarcinomas, surgically obtained with matching normal tissue. All patients were of Northern European descent. Total RNA was isolated from surgical samples and hybridized to Affymetrix HuGene FL arrays as in Example 1.

TABLE 3

Tissue sample origin.

| Patient number | Age in years | Normal sample | Tumor sample |
|---|---|---|---|
| 87 | 57 | Endometrium | Grade III |
| 106 | 65 | Benign tumor | Grade III |
| 119 | 75 | Endometrium | Grade III |
| 122 | 75 | Endometrium | Grade III |

TABLE 4

Genes expresses in normal v. endometrial tumor

| | normal | tumor |
|---|---|---|
| Transcripts detected | 989 | 835 |
| Unique transcripts | 318 | 164 |
| Shared detected | 671 | 671 |
| Shared absent | 2736 | 2736 |

TABLE 5

Genes differentially expressed in endometrial tumors

| Present in Normals/ Absent in Tumors | Absent in Normals/Present in Tumors |
|---|---|
| KIAA0367 | KIAA0119 Platelet activating factor acetylhydrolase 1B gamma-subunit UDP-galactose transporter related isozyme High mobility group protein (HMG-1) Lamin B |

TABLE 6

Genes differentially expressed by at least 4 fold in endometrial tumors

| | |
|---|---|
| Alpha topoisomerase truncated-form | Cyclin-selective ubiguitin carrier |
| Connexin | Carcinoma-associated antigen |
| PKC zeta, thymidine kinase +2 | p78 |
| Keratin 7 | Thyroid receptor interactor (TRIP7) |
| NGAL | Nucleolar protein p40 |
| Gastrointestinal tumor-associated antigen | Sm protein F |
| Cyclin A1 | Ezrin |
| Placental bikunin | Cycstatin B |
| SIX1 | Placental protein 15 |
| Chaperonin 10 | Retinoic acid inducible factor |
| Diazepam binding inhibitor | Splicing factor SRp30c |
| Histone H2B.1 | MLN62 |
| Nm23 | BST-2 |
| Thymosin beta-10 | Ribosomal protein L3 |
| Nuclear localization sequence receptor hSRP1alpha | PAX8 |
| Stromelysin 3 | Transformation-sensitive protein |
| Tumor rejection antigen gp96 | Mitochondrial matrix protein P1 |
| Inositol polyphosphate 5-phosphatase, beta-glucuronidase | HSP 90 |
| DM kinase, Flt4 tyrosine kinase, ERK1, protein serine/threonine kinase, Protein Kinase Ht31, creatine kinase-B | Oncoprotein 18 |
| KIAA0015, 172, 136, 092, 073, 382, 263, 084, 239, Unknown - 2 | PDGF receptor, steroid hormone receptor Ner-I |
| Glycine-rich RNA binding protein | Splicing factor, SF1-Bo isoform |
| Homeotic Protein P12 | Serum response factor (SRF), ERF-2, guanine nucleotide regulatory factor (LFP40), PSE-binding factor PTF delta subunit |
| Non-muscle alpha-actinin | Collagen VI alpha-2 |
| Cisplatin resistance associated alpha protein (hCRA alpha) | MTG8a |
| Serum constituent protein (MSE55) | MADER |
| CDC42 GTPase-activating protein | ARP-1 |
| Guanine nucleotide-binding regulatory protein (G-y-alpha)) | HOX 5.1 |
| Ubiquitin-activating enzyme E1 related protein | p126 (ST5) |
| HNF-3/fork-head homolog-3 HFH-3 | Archain |
| | PKD1 |
| | Bcl-6 |
| | Cyclin 1 |
| | SATB1 |
| | HCG V |

Example 3

Matched normal tissue and adenocarcinoma or clear cell carcinomas ranging from Grade I to III were collected from more than 10 patients. Total RNA was used as starting material for the preparation of fluorescently labeled nucleic acid targets from all of the samples. The labeled targets were hybridized to high-density DNA microarrays containing probes representing ~6800 full-length human genes (Affymetrix, Inc., Santa Clara, Calif.). Sample preparation and hybridization was carried out in a manner similar to the examples and description above. Differential gene expression patterns in both of the subtypes of endometrial cancer were identified.

TABLE 7

Differential expression in endometrial cancers

| | Normal | Adenocarcinoma | Clear cell carcinoma |
|---|---|---|---|
| MIF | − | + | |
| Cyclin A1 | − | + | |

TABLE 7-continued

Differential expression in endometrial cancers

| | Normal | Adenocarcinoma | Clear cell carcinoma |
|---|---|---|---|
| MRG1 | + | − | |
| HOX1 | + | − | |
| Alpha 2 collagen type VI | + | +/− | |
| Adducin | + | +/− | +/− |
| Cyclin B | +/− | + | |
| PKC zeta | +/− | + | |
| Calponin | + | | − |
| Caldesmon | + | | − |
| Keratin K17 | − | | + |
| ESE-1b | − | | + |
| HMG1 | − | | + |
| LAMB3 | +/− | | + |
| Laminin SB3 | +/− | | + |
| Osteopontin | +/− | | + |
| decorin | + | | +/− |

([−], no expression observed; [+], expression observed; [+/−], expression observed but lower than corresponding matched sample).

Example 4

GeneCluster The application of self-organizing maps, a type of mathematical cluster analysis that is particularly well suited for recognizing and classifying features in complex, multidimensional data. The method has been implemented in a publicly available computer package, GENECLUSTER, that performs the analytical calculations and provides easy data visualization. GENECLUSTER was used to organize the genes into biologically relevant clusters SOMs have a number of features that make them particularly well suited to clustering and analysis of gene expression patterns. They are ideally suited to exploratory data analysis, allowing one to impose partial structure on the clusters (in contrast to the rigid structure of hierarchical clustering, the strong prior hypotheses used in Bayesian clustering, and the nonstructure of k-means clustering) and facilitating easy visualization and interpretation. SOMs have good computational properties and are easy to implement, reasonably fast, and scalable to large data sets. SOMs have been well studied and empirically tested on a wide variety of problems.

The microarray data, though voluminous, can be analyzed by pattern recognition (clustering) software to aid in deriving lists of genes that distinguish and characterize disease versus normal biopsies, thus shedding light on molecular genetic profiles and ultimately the mechanism of the disease under study. Techniques used for clustering include self-organizing maps (SOM), Bayesian, hierarchical, and k-means. SOM was selected for our analysis because of advantages in initial exploration of the data allowing the operator to impose partial structure on the clusters 9. Other advantages of SOM include good computational properties, computational speed and easy implementation.

GeneCluster Analysis was conducted on endometrial cancer samples. It reveals that expression patterns delineating normal from tumor tissues. Hierarchical clustering using GenExplore distingushed majority of the normal and tumor tissues.

CONCLUSION

From the foregoing it can be seen that the advantage of the present invention is that samples that differ from one another in multiple variables can be analyzed in such a way as to account for the variables and to focus on elements that are under investigation, such as disease state for example. Comparison of matched samples eliminates gene expression differences that are the result of changes in variables that are not of interest. The gene expression differences that remain can be attributed with a high degree of confidence to the unmatched variation. The gene expression differences thus identified can be used for example to diagnose disease, identify physiological state, design drugs, and monitor therapies.

All publications and patent applications cited above are incorporated by reference in their entirety for all purposes to the same extent as if each individual publication or patent application were specifically and individually indicated to be so incorporated by reference. Although the present invention has been described in some detail by way of illustration and example for purposes of clarity and understanding, it will be apparent that certain changes and modifications may be practiced within the scope of the appended claims.

What is claimed is:

1. A method for diagnosing endometrial cancer in an endometrial tissue sample comprising:

obtaining a gene expression profile from the endometrial tissue sample wherein expression of the following genes is measured: KIAA0367, KIAA0119, platelet activating factor acetylhydrolase 1B gamma-subunit, UDP-galactose transporter related ioszyme, HMG-1 and Lamin B; and identifying the sample as being cancerous if KIAA0367 expression is downregulated as compared to a normal control sample and KIAA0119, platelet activating factor acetylhydrolase 1B gamma-subunit, UDP-galactose transporter related ioszyme, HMG-1 and Lamin B expression is upregulated as compared to a normal control sample.

* * * * *